United States Patent [19]

Gross et al.

[11] 4,202,881

[45] May 13, 1980

[54] HAIR SHAMPOO AND CONDITIONING LOTION

[75] Inventors: Paul Gross; Eugen Konrad, both of Darmstadt, Fed. Rep. of Germany; Herbert Mager, Fribourg, Switzerland

[73] Assignee: Wella AG, Darmstadt, Fed. Rep. of Germany

[21] Appl. No.: 952,857

[22] Filed: Oct. 19, 1978

Related U.S. Application Data

[63] Continuation-in-part of Ser. No. 743,290, Nov. 18, 1976, Pat. No. 4,134,412.

[30] Foreign Application Priority Data

Jun. 18, 1976 [DE] Fed. Rep. of Germany ....... 2627419

[51] Int. Cl.$^2$ ................................................ A61K 7/06
[52] U.S. Cl. ........................................................ 424/70
[58] Field of Search ........................................... 424/70

[56] References Cited

U.S. PATENT DOCUMENTS

| | | | |
|---|---|---|---|
| 3,879,376 | 4/1975 | Vanlerberghe et al. | 424/47 |
| 3,904,748 | 9/1975 | Eckert et al. | 424/71 |
| 4,035,267 | 7/1977 | Gleckler et al. | 424/71 |
| 4,134,412 | 1/1979 | Gross et al. | 424/71 |

OTHER PUBLICATIONS

Chemical Abstracts, vol. 59 (1963), p. 3465c.

*Primary Examiner*—V. D. Turner
*Attorney, Agent, or Firm*—Michael J. Striker

[57] ABSTRACT

A process for shampooing and/or conditioning the hair by applying to the hair a lotion containing a shampoo and/or conditioning agent including an aqueous or aqueous-alcoholic solution, emulsion or gel containing a water soluble salt of chitosan.

8 Claims, No Drawings

HAIR SHAMPOO AND CONDITIONING LOTION

CROSS-REFERENCE TO RELATED APPLICATION

This application is a continuation-in-part of the application Ser. No. 743,290 filed Nov. 18, 1976 now U.S. Pat. No. 4,134,412.

BACKGROUND OF THE INVENTION

The invention relates to hair conditioners and hair shampoos which contain water soluble salts of chitosan.

Hair conditioners have the object of improving the general condition of the hair and customarily are oil-in-water emulsions which are based on oily, semi-solid or solid compounds, such as for instance paraffin oil, Vaseline, wool fat, wool fatty alcohols, fatty acid esters and hydrocarbon waxes.

As emulsifiers for the emulsion ordinarily quaternary ammonium compounds are used such as oxyethylalkylammoniumphosphates, alkyltrimethylammoniumchlorides, dialkyldimethylammoniumchlorides, alkyldimethylbenzylammoniumchlorides and alkylpyridiniumchlorides. These compounds are used either alone or in combination with non-ionic emulsifiers. Also, aqueous solutions or aqueous gels containing quaternary ammonium compounds are frequently used as hair conditioners.

Hair shampoos customarily contain anionic surface active agents, such as for instance fatty alcohol sulfates, fatty alcohol ethersulfates, fatty acid monoglyceride sulfates, alkylarylsulfates and sulfosuccinates. Special hair shampoos are compositions which contain nonionic, cationic, ampholytic surface active agents or mixtures of these agents as active wash components. Among the nonionic surface active agents there may for instance be mentioned nonylphenolpolyglycol ethers, sorbitan fatty acid esters, sorbitan polyoxyalkylene fatty acid esters, fatty acid ethoxylates and fatty alcohol ethoxylates.

Representative of the cationic surface active agents are for instance alkyldimethylbenzyl ammoniumchlorides, pentaoxyethyl ammoniumchlorides, alkyltrimethyl ammoniumchlorides, alkyldimethyl ammoniumsaccharinates and alkyldimethyl dichlorobenzylammoniumchlorides.

As ampholytic surface active agents there can be mentioned the amidoalkylbetaines, sulfobetaines and N-Alkyl-$\beta$-aminopropionic acid.

It is also known to add to shampoos, small amounts of compounds which are intended to effect a better conditioning of the hair. Apart from various other compounds there are frequently used for this purpose quaternary ammonium compounds and oxethylated alkylolamides.

It has, however, been found during practical application that the prior art hair conditioners and hair shampoos are not entirely satisfactory regarding their conditioning effect, in particular regarding the touch, gloss and combing properties of the hair.

The present invention has therefore the object to provide for a process by which an improved conditioning of the hair is possible during or without shampooing the hair and, if desired, together with a dyeing of the hair.

SUMMARY OF THE INVENTION

This is accomplished in the process of the invention by adding to the hair conditioner and/or hair shampoo a water-soluble salt of a chitosan. As a result of this addition the conditioning effect is substantially improved and particularly the combing properties and the gloss and touch of the hair are improved even in damaged hair.

The chitosan is a high polymer amine and adapted to form salts with acids. It is made by alkaline deacetylation of chitin. The complete deacetylation is difficult since the alkali during the reaction penetrates the chitin particles only imperfectly. A virtually acetyl-free chitin, that is pure chitosan, can be obtained only by repeated alkali treatment or by fractionating. The chitosan commercially available therefore constitutes a more or less deacylated product with a chitosan contents of about 70 to 90% by weight. These commercial products as well as products with a higher contents of chitosan can be used for the purposes of the invention equally well.

By neutralization of the free amino groups of the chitosan with acids the corresponding salts can be obtained. According to the present invention, however, the salts can only be employed if they are soluble in water. Suitable acids for making the salts are for instance hydrochloric acid, formic acid, acetic acid, lactic acid, glycolic acid, malonic acid, benzoic acid, adipic acid, nitrilotriacetic acid, ethylenediaminetetraacetic acid, p-hydroxybenzoic acid, citric acid, benzenedisulfonic acid, salicylic acid and chlorosulfonic acid. Preferred for the purposes of the invention are the salts of formic acid, acetic acid and lactic acid.

The amount of acid preferably is chosen to obtain sufficient neutralization of the free amino groups of the initial chitosan. Thus for instance in order to form an aqueous solution of 1 gram of chitosan (having 90% of free amino groups) 3.36 grams of 10% acetic acid are necessary. A small excess of the acid during the neutralization has no effect on the usefulness of the final compound.

The compounds of the invention are aqueous solution, emulsions or gels which are characterized by their contents of water soluble salts of chitosan. The concentration of the salts in the composition should preferably be between about 0.5 and 6.0% by weight. However, depending on the total composition there may also occasionally be used higher or lower amounts of chitosan salt.

The hair conditioners used in the process of the invention, insofar as the general conditioning agents are concerned, contain the conventional agents of this kind as above already mentioned. Regarding the shampoos used in the process of the invention those containing nonionic, cationic or amphoteric surface active agents have been found to be particularly suitable. These are then the special hair shampoo compositions which also have been mentioned above.

It should be understood that the hair conditioners and shampoos used in the process of the invention may also contain the conventional cosmetic additives such as for instance perfume oils, bactericidal and fungicidal compounds, turbidity agents, thickeners and directly applicable dyestuffs.

Among the conventional cosmetic dyestuffs which can be used singly or in mixture there are for instance mentioned the following classes: aromatic nitro dyestuffs (e.g. 1,4-diamino-2-nitrobenzene), azo dyestuffs (e.g. Acid Brown 4), anthraquinone dyestuffs (e.g. C.I. Disperse Violet 4) and triphenylmethane dyestuffs (e.g. Basic Violet 1). The dyestuffs of these types depending on the kind of substituents may have acid, nonionic or basic character. Their total concentration normally is between about 0.05 and 2.0% by weight.

In general the application of the compositions in the process of the invention is effected by applying the solution, etc. to the hair, permitting it to act on the hair for about 3 to 10 minutes and then removing it again by rinsing.

PREFERRED EXAMPLES OF THE INVENTION

The following examples will further illustrate the invention without intention of any limitation.

A. Hair conditioners

EXAMPLE 1

Emulsion consisting of

| | |
|---|---|
| 3.0 g | stearylalcohol |
| 1.0 g | adeps lanae |
| 1.0 g | Vaseline |
| 0.3 g | chitosan (with 90% free amino groups) |
| 0.76 g | formic acid, 10% conc. |
| 2.0 g | tris-(oligooxyethyl)-octadecyl-ammoniumphosphate, 50% conc. |
| 91.94 g | water, fully desalted |
| 100.00 g | |

EXAMPLE 2

Emulsion consisting of

| | |
|---|---|
| 4.0 g | cetylstearyl alcohol |
| 0.3 g | chitosan (with 90% free amino groups) |
| 1.48 g | lactic acid, 10% conc. |
| 2.5 g | cocopentaethoxymethyl ammoniumchloride |
| 1.0 g | sorbitan monopalmitate with 20 mol ethylenoxide |
| 90.72 g | water, fully desalted |
| 100.00 g | |

EXAMPLE 3

Emulsion consisting of

| | |
|---|---|
| 5.0 g | cetyl alcohol |
| 3.0 g | lauryldimethyl benzyl ammoniumchloride, 35% conc. |
| 1.2 g | dimethylcarboxymethylene propylene-amidostearate betaine, 35% conc. |
| 0.45 g | chitosan (with 90% free amino groups) |
| 1.14 g | formic acid, 10% conc. |
| 89.21 g | water, fully desalted |
| 100.00 g | |

EXAMPLE 4

Gel consisting of

| | |
|---|---|
| 0.6 g | hydroxypropylmethylcelluse |
| 2.1 g | chitosan (with 90% free amino groups) |
| 5.3 g | formic acid, 10% conc. |
| 0.5 g | laurylpyridiniumchloride |
| 91.5 g | water, fully desalted |
| 100.0 g | |

EXAMPLE 5

Emulsion consisting of

| | |
|---|---|
| 4.0 g | cetylalcohol |
| 1.5 g | Vaseline |
| 2.5 g | tris-(oligooxyethyl)-octadecyl-ammoniumphosphate, 50% conc. |
| 0.3 g | chitosan (with 90% free amino groups) |
| 0.75 g | formic acid, 10% conc. |
| 0.1 g | C.I. Basic Violet 1 |
| 90.85 g | water, fully desalted |
| 100.00 g | |

Normally about 35 g of the hair conditioners illustrated in Examples 1 to 5 are spread throughout the washed hair and are then permitted to act on the hair for 3 to 5 minutes followed by rinsing. As a result there is obtained an excellent touch, gloss and combing property of the hair.

B. Shampoos

EXAMPLE 6

Solution consisting of

| | |
|---|---|
| 50.0 g | dimethyl carboxymethylene propylene amidostearate betaine, 30% conc. |
| 2.0 g | chitosan (with 90% free amino groups) |
| 2.2 g | lactic acid, 90% conc. |
| 45.8 g | water, fully desalted |
| 100.0 g | |

EXAMPLE 7

| | |
|---|---|
| 40.0 g | dimethyl carboxymethylene propylene amidostearate betaine, 35% conc. |
| 2.0 g | chitosan (with 90% free amino groups) |
| 2.2 g | lactic acid, 90% conc. |
| 3.5 g | coconut oil acid diethanolamide |
| 52.3 g | water, fully desalted |
| 100.0 g | |

EXAMPLE 8

Solution consisting of

| | |
|---|---|
| 40.0 g | dimethyl carboxymethylene propylene amidostearate betaine, 35% conc. |
| 3.0 g | chitosan (with 90% free amino groups) |
| 7.6 g | formic acid, 10% conc. |
| 5.0 g | cetyltrimethylammoniumchloride, 50% conc. |
| 44.4 g | water, fully desalted |
| 100.0 g | |

EXAMPLE 9

Solution (turbid) consisting of

| | |
|---|---|
| 40.0 g | dimethyl carboxymethylene propylene amidostearate betaine, 35% conc. |
| 2.0 g | chitosan (with 90% free amino groups) |
| 2.2 g | lactic acid, 90% conc. |

| | -continued |
|---|---|
| 5.0 g | cetyltrimethylammoniumchloride, 50% conc. |
| 2.0 g | triethylene glycoldistearate |
| 48.8 g | water, fully desalted |
| 100.0 g | |

Normally the hair is washed with about 15 to 20 grams of the shampoo illustrated in Examples 6 to 9. Thereafter the hair is rinsed with water. As a result the hair is excellently conditioned in respect of touch, gloss and combing properties.

C. Combined shampoo and dye

EXAMPLE 10

Solution consisting of

| | |
|---|---|
| 40.0 g | dimethyl carboxymethylene propylene amidostearate betaine, 35% conc. |
| 2.0 g | chitosan (with 90% free amino groups) |
| 5.06 g | formic acid, 10% conc. |
| 3.5 g | coconut acid diethanolamide |
| 1.0 g | hair orange II B (C.I. 76 540), 1% conc. aqueous solution |
| 48.44 g | water, fully desalted |
| 100.00 g | |

Regarding Example 10, normally the hair is shampooed with about 15 to 20 g of the composition. After permitting the composition to act on the hair for about 5 to 10 minutes the hair is subjected to rinsing. As a result the hair gets a yellow-orange shade and is excellently conditioned.

Regarding the combination of a dye with a hair conditioner reference is made to above Example 5.

All percentages in the above examples are percentages by weight.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A process of shampooing and conditioning human hair which comprises applying to the hair a lotion comprising an aqueous or aqueous-alcoholic solution, emulsion or gel containing 0.05 to 6% by weight of a water soluble salt of chitosan, said chitosan salt having been prepared by reacting chitosan or a chitin product containing about 70 to 90% by weight of chitosan with a sufficient amount of acid to neutralize the free amino groups present in said chitosan and to form a water soluble salt thereof.

2. The process of claim 1, wherein said lotion is permitted to act on the hair for about 3 to 10 minutes and is thereafter removed by rinsing the hair.

3. The process of claim 1, wherein said lotion contains about 10–20% of a surface active agent of the cationic, nonionic or ampholytic type.

4. The process of claim 1, wherein said lotion is applied onto the hair in an amount of about 35 grams, said lotion containing about 1–5% of cetyl or stearyl alcohol and about 0.5–5% of ammonium phosphate or ammonium chloride.

5. The process of claim 1, wherein said lotion contains about 0.2–5% of a quaternary ammonium compound.

6. The process of claim 1, wherein said lotion contains 0.2–5% of an oxyethylated alkylolamide.

7. The process of claim 1, wherein said lotion is applied onto the hair in an amount of about 15–20 grams, said lotion containing 10–20% of a mono or distearate of mono or polyethyleneglycol.

8. The process of claim 7, wherein said lotion contains 10–20% of a surface active agent of the cationic, nonionic or ampholytic type.